(12) United States Patent
Goraltchouk et al.

(10) Patent No.: US 8,951,596 B2
(45) Date of Patent: Feb. 10, 2015

(54) IMPLANTS AND METHODS FOR MANUFACTURING SAME

(71) Applicant: Allergan, Inc., Irvine, CA (US)

(72) Inventors: Alexei Goraltchouk, Rensselaer, NY (US); Dennis Van Epps, Goleta, CA (US); Thomas E. Powell, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/942,104

(22) Filed: Jul. 15, 2013

(65) Prior Publication Data

US 2013/0302511 A1  Nov. 14, 2013

Related U.S. Application Data

(63) Continuation of application No. 12/897,498, filed on Oct. 4, 2010, now abandoned.

(60) Provisional application No. 61/252,330, filed on Oct. 16, 2009.

(51) Int. Cl.
| | |
|---|---|
| *A61F 2/52* | (2006.01) |
| *B05D 3/10* | (2006.01) |
| *B05D 3/02* | (2006.01) |
| *B05D 1/38* | (2006.01) |

(Continued)

(52) U.S. Cl.
CPC . *A61F 2/12* (2013.01); *A61L 27/30* (2013.01); *A61L 27/56* (2013.01); *A61L 2400/18* (2013.01)
USPC ........... 427/2.24; 427/2.1; 427/202; 427/335; 623/7

(58) Field of Classification Search
USPC .............................................. 427/2.24; 623/7
See application file for complete search history.

(56) References Cited

U.S. PATENT DOCUMENTS

| | | | |
|---|---|---|---|
| 2,324,735 | A | 1/1941 | Spanel |
| 2,805,208 | A | 9/1957 | Roche |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Alvarez et al, "Synthesis of Macro/Mesoporous Silica and Carbon Monoliths by Using a Commercial Polyurethane Foam as Sacrificial Template", Materials Letters, 61, 2378-2381 (2007).

(Continued)

*Primary Examiner* — Cachet Sellman
(74) *Attorney, Agent, or Firm* — Linda Allyson Nassif

(57) ABSTRACT

Implantable prosthesis, components of prosthesis, and methods of making same are provided. The methods generally include the steps of providing an implant shell, applying a curable fluid composition to the shell to form a coating thereon and applying a particulate component to the composition. The composition is a mixture, for example, an emulsion, containing a silicone-based elastomer dispersion and droplets of a suspended leachable agent. After the elastomer is stabilized and cured, the particulate component and leachable agent are removed, resulting in an implantable member having a porous, open-cell surface texture designed to be effective in reducing incidence of capsular formation or contraction.

20 Claims, 3 Drawing Sheets

(51) Int. Cl.
*A61F 2/12* (2006.01)
*A61L 27/30* (2006.01)
*A61L 27/56* (2006.01)

(56) References Cited

U.S. PATENT DOCUMENTS

| | | |
|---|---|---|
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras et al. |
| 3,852,832 A | 12/1974 | McGhan |
| 3,934,274 A | 1/1976 | Hartley, Jr. |
| 4,034,751 A | 7/1977 | Hung |
| 4,157,085 A | 6/1979 | Austad |
| 4,231,979 A | 11/1980 | White et al. |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Baumann et al. |
| 4,592,755 A | 6/1986 | Penton |
| 4,608,396 A | 8/1986 | Baumann et al. |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Baumann et al. |
| 4,648,880 A | 3/1987 | Braumann |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo et al. |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iverson |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A * | 12/1996 | Seare, Jr. .................. 424/400 |
| 5,605,693 A | 2/1997 | Seare |
| 5,607,473 A | 3/1997 | Weber-Unger |
| 5,624,674 A | 4/1997 | Seare, Jr. |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle et al. |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,964,803 A | 10/1999 | Iversen |
| 5,965,076 A | 10/1999 | Banks |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |

(56) References Cited

U.S. PATENT DOCUMENTS

| | | | |
|---|---|---|---|
| 6,531,523 B1 | 3/2003 | Davankov et al. | |
| 6,544,287 B1 | 4/2003 | Johnson | |
| 6,602,452 B2 | 8/2003 | Schuessler | |
| 6,605,116 B2 | 8/2003 | Falcon | |
| 6,638,308 B2 | 10/2003 | Corbitt, Jr. | |
| 6,673,285 B2 | 1/2004 | Ma | |
| 6,692,527 B1 | 2/2004 | Bellin | |
| 6,755,861 B2 | 6/2004 | Nakao | |
| 6,802,861 B1 | 10/2004 | Hamas | |
| 6,811,570 B1 | 11/2004 | Gehl | |
| 6,818,673 B2 | 11/2004 | Ferguson | |
| 6,875,233 B1 | 4/2005 | Turner | |
| 6,881,226 B2 | 4/2005 | Corbitt, Jr. | |
| 6,900,055 B1 | 5/2005 | Fuller et al. | |
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 7,081,135 B2 | 7/2006 | Smith et al. | |
| 7,081,136 B1 | 7/2006 | Becker | |
| 7,105,116 B2 | 9/2006 | Bellin | |
| 7,169,180 B2 | 1/2007 | Brennan | |
| 7,192,450 B2 | 3/2007 | Brauker et al. | |
| 7,244,270 B2 | 7/2007 | Lesh | |
| 7,268,169 B2 | 9/2007 | Hirayma et al. | |
| 7,323,208 B2 | 1/2008 | Ma | |
| 7,476,249 B2 | 1/2009 | Frank | |
| 7,520,896 B2 | 4/2009 | Benslimane | |
| 7,547,393 B2 | 6/2009 | Ramaswamy et al. | |
| 7,625,405 B2 | 12/2009 | Purkait | |
| 7,632,228 B2 | 12/2009 | Brauker et al. | |
| 7,632,291 B2 | 12/2009 | Stephens | |
| 7,641,688 B2 | 1/2010 | Lesh | |
| 7,645,475 B2 | 1/2010 | Prewett | |
| 8,202,317 B2 | 6/2012 | Becker | |
| 8,313,527 B2 | 11/2012 | Powell et al. | |
| 8,377,127 B2 * | 2/2013 | Schuessler | 623/8 |
| 8,487,012 B2 | 7/2013 | Goraltchouk et al. | |
| 8,506,627 B2 | 8/2013 | Van Epps et al. | |
| 8,546,458 B2 | 10/2013 | Thompson et al. | |
| 2002/0038147 A1 | 3/2002 | Miller | |
| 2002/0193885 A1 | 12/2002 | Legeay | |
| 2003/0036803 A1 | 2/2003 | McGhan | |
| 2003/0093151 A1 | 5/2003 | Zhang | |
| 2003/0105469 A1 | 6/2003 | Karmon | |
| 2003/0205846 A1 | 11/2003 | Bellin | |
| 2003/0208269 A1 | 11/2003 | Eaton et al. | |
| 2004/0010225 A1 | 1/2004 | Schuessler | |
| 2004/0115241 A1 | 6/2004 | Calhoun | |
| 2004/0127985 A1 | 7/2004 | Bellin | |
| 2004/0143327 A1 | 7/2004 | Ku | |
| 2004/0148024 A1 | 7/2004 | Williams | |
| 2004/0153151 A1 | 8/2004 | Gonzales | |
| 2004/0176493 A1 | 9/2004 | Ferguson | |
| 2004/0213986 A1 | 10/2004 | Kim et al. | |
| 2005/0055093 A1 | 3/2005 | Brennan | |
| 2005/0070124 A1 | 3/2005 | Miller et al. | |
| 2005/0122169 A1 | 6/2005 | Watanabe | |
| 2005/0143480 A1 * | 6/2005 | Hirayama et al. | 521/154 |
| 2005/0196452 A1 | 9/2005 | Boyan et al. | |
| 2005/0216094 A1 | 9/2005 | Prewett | |
| 2005/0251083 A1 | 11/2005 | Carr-Brendel et al. | |
| 2006/0002810 A1 | 1/2006 | Grohowski | |
| 2006/0036266 A1 | 2/2006 | Sulmanidze et al. | |
| 2006/0036320 A1 | 2/2006 | Job | |
| 2006/0136056 A1 | 6/2006 | Wohl | |
| 2006/0224239 A1 | 10/2006 | Tiahrt | |
| 2006/0229721 A1 | 10/2006 | Ku | |
| 2006/0235094 A1 * | 10/2006 | Habibi-Naini | 521/50 |
| 2006/0246121 A1 | 11/2006 | Ma et al. | |
| 2007/0093911 A1 | 4/2007 | Fricke | |
| 2007/0104693 A1 | 5/2007 | Quijano | |
| 2007/0104695 A1 | 5/2007 | Quijano | |
| 2007/0116735 A1 | 5/2007 | Calhoun | |
| 2007/0135916 A1 | 6/2007 | Maxwell | |
| 2007/0154525 A1 | 7/2007 | Calhoun | |
| 2007/0190108 A1 | 8/2007 | Datta et al. | |
| 2007/0198085 A1 | 8/2007 | Benslimane | |
| 2008/0009830 A1 | 1/2008 | Fujimoto et al. | |
| 2008/0071371 A1 | 3/2008 | Elshout | |
| 2008/0075752 A1 | 3/2008 | Ratner et al. | |
| 2008/0154366 A1 | 6/2008 | Frank | |
| 2008/0241212 A1 | 10/2008 | Moses | |
| 2008/0268019 A1 | 10/2008 | Badylak et al. | |
| 2008/0312739 A1 | 12/2008 | Agerup | |
| 2009/0045166 A1 | 2/2009 | Li | |
| 2009/0082864 A1 | 3/2009 | Chen | |
| 2009/0087641 A1 | 4/2009 | Favis et al. | |
| 2009/0093878 A1 | 4/2009 | Glicksman | |
| 2009/0118829 A1 * | 5/2009 | Powell et al. | 623/8 |
| 2009/0125107 A1 | 5/2009 | Maxwell | |
| 2009/0169716 A1 | 7/2009 | Linhardt | |
| 2009/0198331 A1 | 8/2009 | Kesten et al. | |
| 2009/0198332 A1 | 8/2009 | Becker | |
| 2009/0198333 A1 | 8/2009 | Becker | |
| 2010/0042211 A1 * | 2/2010 | Van Epps et al. | 623/8 |
| 2010/0292790 A1 * | 11/2010 | Stroumpoulis et al. | 623/8 |
| 2011/0035004 A1 | 2/2011 | Maxwell | |
| 2011/0054605 A1 | 3/2011 | Becker | |
| 2011/0093069 A1 | 4/2011 | Goraltchouk et al. | |
| 2011/0106249 A1 | 5/2011 | Becker | |
| 2011/0117267 A1 | 5/2011 | Powell et al. | |
| 2011/0196488 A1 | 8/2011 | Goraltchouk et al. | |
| 2011/0196489 A1 | 8/2011 | Van Epps et al. | |
| 2011/0276133 A1 | 11/2011 | Liu et al. | |
| 2011/0276134 A1 | 11/2011 | Manesis et al. | |
| 2011/0278755 A1 | 11/2011 | Liu et al. | |
| 2011/0282444 A1 | 11/2011 | Liu et al. | |
| 2011/0309541 A1 | 12/2011 | Thompson et al. | |
| 2011/0313073 A1 | 12/2011 | Goraltchouk et al. | |
| 2012/0004722 A1 | 1/2012 | Goraltchouk et al. | |
| 2012/0041555 A1 | 2/2012 | Manesis et al. | |
| 2012/0077010 A1 | 3/2012 | Manesis et al. | |
| 2012/0077012 A1 | 3/2012 | Liu et al. | |
| 2012/0077891 A1 | 3/2012 | Liu et al. | |
| 2012/0101574 A1 | 4/2012 | Goraltchouk et al. | |
| 2012/0245685 A1 | 9/2012 | Yu | |
| 2012/0321777 A1 | 12/2012 | Stroumpoulis et al. | |
| 2013/0013062 A1 | 1/2013 | Thompson et al. | |
| 2013/0023987 A1 | 1/2013 | Liu et al. | |
| 2013/0032962 A1 | 2/2013 | Liu et al. | |
| 2013/0053956 A1 | 2/2013 | Powell et al. | |
| 2013/0158657 A1 | 6/2013 | Nofrey et al. | |
| 2013/0209661 A1 | 8/2013 | Goraltchouk et al. | |
| 2013/0245148 A1 | 9/2013 | Thompson et al. | |
| 2013/0295379 A1 | 11/2013 | Goraltchouk et al. | |
| 2013/0310934 A1 | 11/2013 | Van Epps et al. | |

FOREIGN PATENT DOCUMENTS

| | | |
|---|---|---|
| EP | 0522585 | 1/1993 |
| EP | 1532942 | 5/2005 |
| FR | 2840617 | 12/2003 |
| JP | 2003-062062 | 4/2003 |
| JP | 2007-029717 | 8/2007 |
| WO | 98/10803 | 3/1998 |
| WO | 00/24437 | 5/2000 |
| WO | 2004/037318 | 5/2004 |
| WO | 2004/062531 | 7/2004 |
| WO | 2006/133366 | 12/2006 |
| WO | 2009/061672 | 5/2009 |
| WO | 2009/110917 | 9/2009 |
| WO | 2011/094155 | 8/2011 |
| WO | 2011/097499 | 8/2011 |

OTHER PUBLICATIONS

Barnsley et al., "Textured Surface Breast Implants in the Prevention of Capsular Contracture Among Breast Augmentation Patients: A Meta-Analysis of Randomized Controlled Trials", Plastic and Reconstructuve Surgery, 2006, 117(7), 2182-2190.

Barr et al., "Current Implant Surface Technoogy: An Examination of Their Nanostructure and Their Influence on Fibroblas Alignment and Biocompatibility", Elastic, 2008, 9, 198-217.

(56) References Cited

OTHER PUBLICATIONS

Brauker et al., "Neovascularization of synthetic membranes directed by membrane microarchitecture", Journal of Biomedical Materials Research, 1995, pp. 1517-1524, vol. 29, John Wiley & Sons, Inc.

Brohim et al., "Early Tissue Reaction to Textured Breast Implant Surfaces", Anals of Plastic Surgery, 28(4): 354-362.

Inamaned Aesthetics Brochure, Directions for Use Style 410 Silicone-Filled Breast Implants (2003).

Ma, "Scaffolds for tissue fabrications", Materials Today, 2004, 7, 30-40.

Mikos et al., "Formation of Highly Porous Biodegradable Scaffolds for Tissue Engineeing", Electronic Journal of Biotechnology, 2000, 3(2), 114-119.

Minami et al., "The composition and behavior of capsules around smooth and textured breast implants in pigs", Plastic and Reconstructive Surgery, 2006, 874-884.

Murphy et al. "Salt Fusion: An Approach to Improve Pore Interconnectivity within Tissue Engineering Scaffolds", Tissue Engineering, vol. 8, No. 1, 2002, pp. 43-52 (XP-002588127).

Sharkawy et al. "Engineering the tissue which encapsulates subcutaneous implants", II Plasma—tissue exchange properties, 1998, pp. 586-597, John Wiley & Sons, Inc.

Wei et al., "Macroporous and Nanofibers Polymer Scaffolds and Polymer/Bone-Like Apatite Composite Scaffolds Generated by Sugar Spheres", Journal of Biomedical Materials Research Part A, 2006, 306-315.

Zhang et al., "Macroporous Alumina Monoliths Prepared by Filling Polymer Foams with Alumina Hydrosols", J. Mater Sci., 44, 931-938 (2009).

* cited by examiner

IMPLANTS AND METHODS FOR MANUFACTURING SAME

RELATED APPLICATION

This application is a continuation of U.S. patent application Ser. No. 12/897,498, filed Oct. 4, 2010, which claims priority to U.S. Provisional Patent Application No. 61/252,330, filed on Oct. 16, 2009, the entire disclosures of which are incorporated herein by this specific reference.

BACKGROUND

The present invention generally relates to soft tissue implants and more specifically relates to soft tissue implants designed to enhance fixation in the body and/or alter or reduce capsular formation.

Soft tissue implants, particularly mammary prostheses, are plagued by problems of capsular formation and contracture. Soon after an implant is placed into the body, an inflammatory response begins to deposit a fibrous capsule around the implant. In most cases, particularly for relatively large and smooth implants, the capsule is comprised of highly organized or aligned collagen fibers. As the capsule matures, certain events may trigger the differentiation of fibroblasts to a contractile phenotype (myofibroblasts). In this or similar scenarios, and if the collagen fibers are aligned, capsular contracture may ensue.

Capsular contracture can be debilitating to the patient because of discomfort or even pain caused thereby, can diminish the efficacy of the aesthetic results in both the look and feel of the implant, and can sometimes damage the implant itself. Problems with capsular formation and contracture occur in many implant types such as pacemakers, dura matter substitutes, implantable cardiac defibrillators, pacemaker leads, hernia repair meshes as well as breast and other esthetic implants.

It has been established in the literature that surface texturing of implants often helps to reduce the incidence of capsular contracture when compared to smooth surface implants. Furthermore there is increasing evidence regarding the ability of foam covered implants, for example, polyurethane foam coated implants, to reduce contracture rates. However, polyurethane foam coatings are biodegradable and lose their efficacy once the polyurethane degrades. Further, it can be appreciated that degradation of polyurethane foam into the body is undesirable and potentially unhealthy.

The present invention addresses at least some of these drawbacks of conventional implants.

SUMMARY OF THE INVENTION

The present invention provides implantable members and methods for manufacturing implantable members, for example, prostheses, for example, mammary prostheses, as well as components of prostheses, for example, elastomeric shells, which serve as components of mammary prostheses. The invention further provides coverings, for example, laminates for applying to surfaces of implantable devices. The implantable members have surfaces which may enhance fixation and/or alter or reduce capsular formation. In one aspect of the invention, the textured surfaces are defined by a network of interconnected pores and channels which encourages tissue ingrowth and discourages organization of the collagen capsule. Generally, the pores have, on average, more than two interconnections assuming that the average number of interconnections per pore does not vary significantly.

The method generally comprises the steps of providing an implantable member, for example an implant shell, for example, a conventional smooth silicone-based implant shell, and applying a curable fluid composition to the shell to form a coating thereon. In one embodiment, the composition comprises a silicone-based mixture including a solvent, and a pore-forming material, for example, a leachable agent, dispersed therein. The composition is allowed to stabilize on the shell, for example, by allowing some of the solvent to evaporate out of the composition or allowing a chemical reaction to occur inducing precipitation of the soluble components. Alternatively, stabilization can be achieved during crosslinking of polymerization of the silicone, precipitation of the silicone or pore-forming material of a combination of the above alone or in conjunction with solvent evaporation.

Next, a particulate component, hereinafter sometimes simply referred to as "particles" or a "particle coating", is applied to the composition coating while the composition coating is less than entirely cured, or at least has a stickiness or tackiness capable of retaining the particulate coating.

In some embodiments, the steps of applying a curable fluid composition and applying a particle coating are then repeated, for example, one or more times, for example, three, five or even up to 20 times, until a final coating is applied. The final coating may be a particle coating or a composition coating.

After the final coating of particles or fluid composition is applied to the shell, the coated shell is then subjected to suitable curing conditions to solidify the composition with the particles embedded therein.

In one embodiment, the particulate coating itself is used to stabilize the coating composition, for example, by absorbing some or all of the solvent, increasing the rate of polymerization of crosslinking of the silicone, promoting precipitation of the silicone or porogen, or a combination of one or more of the above.

Once solidified, the leachable agent contained in the composition and the particles embedded therein are then removed from the coating thereby revealing a network of interconnected pores (the structure may include both relatively large pores and relatively smaller pores, for example, micropores) within the cured elastomer. The surface topography created by the processes described herein, when used as a part of an implant at the tissue/implant interface, may be highly effective in altering capsular formation so as to achieve a more preferred morphology, or in reducing or preventing capsular contracture, relative to conventional surface topographies.

Removal of the particles and leachable agent may be accomplished by any suitable means effective to remove these materials from the surrounding elastomer "matrix", and create the desirable surface topography.

For example, the particles and/or leachable agent(s) may be extracted by exposing the coating to one or more suitable mediums capable of dissolving, extracting or otherwise removing the particles and/or leachable agent while leaving the cured elastomer matrix generally intact.

Generally, the particles, which are typically larger in size than the dispersed leachable agent, serve to create cavities or pores in the cured elastomer while the dispersed leachable agent serves to create microcavities or micropores which serve as interconnections between the pores. This network of interconnected pores and micropores facilitates tissue ingrowth, encourages better fixation of the implant in the patient, and discourages organization of the fibrous capsule, which may help reduce or prevent capsule formation and contraction.

BRIEF DESCRIPTION OF THE DRAWINGS

The present invention may be more clearly understood and the aspects and advantages thereof more clearly appreciated with reference to the following detailed description and accompanying drawings of which.

DETAILED DESCRIPTION

Figure 1:
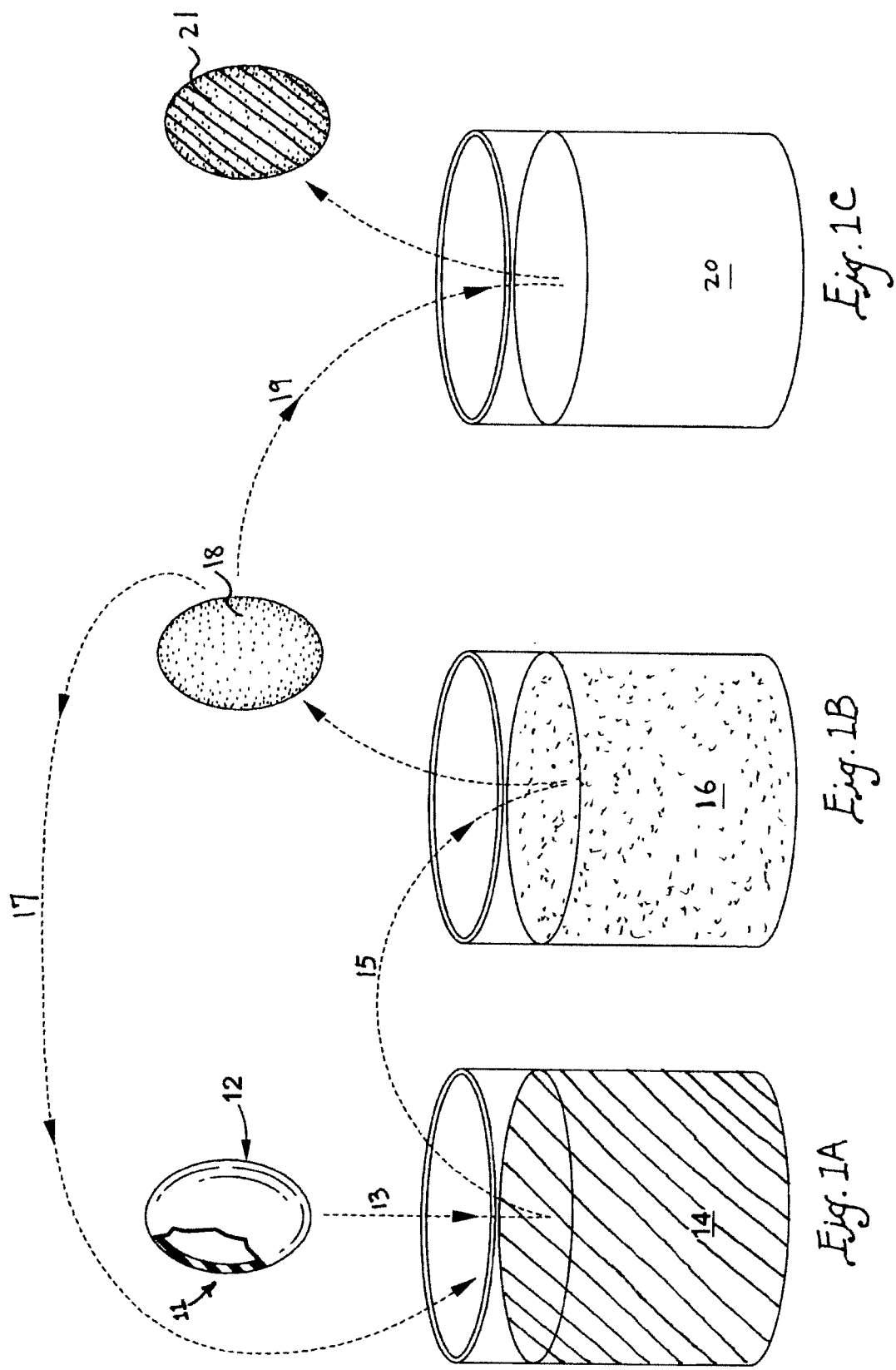
FIGS. 1A-1C represents suitable process steps in a method for manufacturing an elastomeric shell in accordance with an embodiment of the invention.

Accordingly, implantable composite members and methods for manufacturing such implantable composite members are provided.

In one aspect of the invention, the present invention provides an implantable composite member, hereinafter, typically referred to as an "implant", having a surface that renders the implant effective in reducing the occurrence or severity of capsule formation when the implant is placed in the body. In a specific exemplary embodiment that will now be described, the implant is a fillable mammary prosthesis useful in breast reconstruction or breast augmentation. It should be appreciated, however, that the present invention is not limited to mammary prostheses, but is useful in many situations in which an implant is intended to be permanently or temporarily placed in the body and which capsule formation or contraction is to be avoided or impaired.

First, in a method of the invention, an implant member is provided. The implant member may be a fillable, elastomeric implant shell having a configuration of a breast prosthesis. Such shells are intended to be filled, typically, with saline or silicone gel before or after implantation in the breast.

Generally, manufacture of such shells is commonly accomplished by applying a liquid dispersion, for example, a silicone elastomer dispersion, to a mandrel having a desired form. The dispersion generally contains a silicone elastomer and a solvent. The silicone elastomer may be polydimethyl-siloxane, polydiphenyl-siloxane or some combination of these two materials. Typical solvents include xylene, trichloromethane, heptane, hexane, and toluene.

The silicone dispersion forms an elastomeric coating on the mandrel. The coating is cured and the solvent evaporates therefrom. This procedure may be repeated a number of times in order to obtain an implant shell having a desired thickness. This shell may be used as base component for many of the implants of the present invention.

In accordance with one aspect of the invention, an implantable member having a desired surface topography is provided. The method comprises the steps of applying a curable fluid composition to a substrate, for example, a surface of an implant shell described above, applying a particulate material to the composition, and in some instances, repeating these steps to achieve layers, for example, alternating layers of composition and particulates. The composition includes a leachable component to be described elsewhere herein. The composition layers are allowed to stabilize between subsequent applications.

Once the layering steps are completed, the composition is subject to conditions to allow it to at least partially cure. Curing process steps will depend on the materials used. One or more process steps are performed to remove the particles of the particle layer(s) and the leachable component from the elastomer.

The resulting implant has an external surface at least a portion of which is an open-cell porous structure having a topography or porosity that affects capsule formation and/or adhesion of the implant when implanted in a patient.

The curable fluid composition may be in the form of an emulsion, dispersion, solution, suspension or mixture containing an elastomer component, a solvent component and a leachable component.

The elastomer component may be an uncured silicone polymer, for example, a silicone elastomer. For example, in some embodiments, the elastomer component is a room temperature vulcanizing (RTV) silicone elastomer. The elastomer component may be polydimethyl siloxane, polydiphenyl siloxane or a combination of these two. Possible silicone elastomer systems useful in the present invention include, but are not limited to, oxime, platinum or tin catalyst based systems. Alternatively, the elastomer component may be a non-silicone based material.

The solvent component may be any suitable solvent or solvent system, appropriate to the elastomer. Representative examples of solvents include chloroform, acetone, water (buffered saline), dimethyl sulfoxide (DMSO), propylene glycol methyl ether (PM), isopropyl alcohol (IPA), n-propyl alcohol, methanol, ethanol, tetrahydrofuran (THF), dimethylformamide (DMF), dimethyl acetamide (DMAC), N-Methylpyrrolidone (NMP), benzene, toluene, xylene, hexane, cyclohexane, heptane, octane, pentane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and combinations thereof. In one embodiment, the solvent is selected from the group of solvents consisting of xylene, pentane, hexane, heptane, dichloromethane, trichloromethane, toluene, dimethyl sulfoxide, dioxane, NMP, DMAC, and combinations thereof. The solvent component may comprise one or more different solvents. For example, the solvent component may comprise between one and twenty different solvents. Generally, the solvent may comprise any suitable protic or aprotic solvent, mixture or solution thereof.

The leachable component is a leachable material/agent in the form of any suitable solid particulates, semi-solids, composites, gels, for example, hydrogels, liquid droplets, etc. The leachable agent may comprise any suitable polymer, ceramic, metal, composite or combination thereof that can be dissolved or otherwise removed by suitable means from the cured formulation. In some embodiments, the composition comprises one or more different leachable agents. For example, the composition may comprise between one and twenty different types of leachable agents.

The elastomer component can be present in the composition in a range of about 1% to about 99% of volume as part of the total dissolved solids and the leachable agent can be in the range of about 1% to about 99% of volume as part of the total dissolved solids. In a specific embodiment of the invention, the composition includes up to 96% leachable phase. In some embodiments, the elastomer component is present in the composition in a range of about 5% to about 80% and the leachable agent is present in the composition in a range of about 20% to about 95% of total dissolved solids. Generally, the total dissolved solids in the composition can range from about 1% to about 50% by weight in solution.

The ratio of leachable phase to matrix phase in the composition generally affects the porosity of the final cured composition. For example, a greater percentage of leachable component in the composition will produce a composition layer having greater interconnections between pores.

In an exemplary embodiment, the curable fluid composition is in the form of an emulsion, and the leachable agent is present in a concentration of up to about 50% concentration by volume of the emulsion. In some embodiments, the composition comprises a microphase separation containing an elastomer matrix phase and droplets of leachable material in suspended phase, the droplets being about 0.01 μm to about 10,000 μm in diameter, for example, about 1 μm to about 5,000 μm in diameter, for example, about 50 μm to about 400 μm in diameter. After the leachable agent has been leached from the elastomer, voids left behind by the leachable agent will serve as interconnections between voids left by the removed particles.

The leachable agent may be, for example, any material that can be dispersed through the elastomer dispersion (elastomer component/solvent system) and can be removed therefrom once the elastomer component is cured. The leachable agent may be an agent that can be removed from the cured elastomer, for example, by leaching, evaporation, sublimation, dissolution, etc. In an exemplary embodiment, the leachable agent is a water soluble material dispersed throughout the elastomer dispersion.

Typical leachable agent in accordance with the invention may comprise, for example, polyethylene glycol (PEG) (also known as polyoxyethylene), polyalkylene oxides including polyethylene oxide and polyethylene oxide/polypropylene oxide copolymers (also known as poloxamers), polyhydroxyethylmethacrylate, polyvinylpyrrolidone, polyacrylamide and its copolymers, polylactides, polyglycolides, polyanhydrides, polyorthoesters and their copolymers, proteins including albumin, peptides, liposomes, cationic lipids, ionic or nonionic detergents, salts including potassium chloride, sodium chloride and calcium chloride; sugars including galactose, glucose and sucrose; polysaccharides including soluble celluloses, heparin, cyclodextrins and dextran; and any combination thereof.

In some embodiments, the leachable agent is an agent selected from the group of agents consisting of polyvinyl alcohol, polyethylene glycol, polyacrylic acid, polymethacrylate, poly-lactide, polyglycolide, polycaprolatone, polydioxanone; and derivatives, blends, copolymers, terpolymers, and combinations thereof.

In some embodiments, the leachable agent is in the form of droplets of leachable material having diameters in a range of between about 0.01 micron to about 10,000 microns. For example, the leachable agent may be in the form of droplets having diameters in a range of between about 1 micron to about 5,000 microns, for example, in a range of between about 50 microns to about 400 microns.

The particulates of the particle layer comprise any suitable particles which may be removed from the cured elastomer, leaving cavities where the particles had been.

For example, the particles may comprise particles that can be removed from the elastomer by at least one of mechanical abrasion, leaching, evaporation, sublimation, dissolution etc.

In an exemplary embodiment, the particles are a solid, water soluble material. For example, the particles may be material selected from the group of materials consisting of sodium chloride, barium sulfate, potassium nitrate and sodium carbonate.

In addition, the particles may have dimensions and shapes as desired to bring about a resulting topography. For example, the particles may be substantially round or spherical, multi-faceted, angular, or cubic or a combination thereof. The particles may have an average particle size in a range of between about 0.01 micron to about 10,000 microns, for example, in a range of between about 10 microns to about 6,000 microns, for example, in a range of between about 100 microns to about 900 microns.

In some embodiments, the size of the particles is approximately proportional to the thickness of the composition coating on which they are deposited, or the thickness of adjacent interconnecting composition coatings in a multilayered embodiment. For example, particles with an average size of about 500 micron could be used in conjunction with a composition layer having a thickness of about 100 microns to about 500 microns. For particles with an average size of about 300 microns, a composition layer of about 50 microns to about 400 microns could be used.

Figure 2:
FIGS. 2-6 are cross-sectional views of components of the shell during various steps of the process for making the shell shown in FIGS. 1A-1C.

FIGS. 1A-1C illustrate an exemplary process for making an implant in accordance with an embodiment of the invention. Step one is illustrated in 1A. In FIG. 1A, a flexible, elastomeric implantable member 12 is depicted. The partial cross sectional view 11 of the elastomeric implant member 12 is shown in FIG. 1A as well as FIG. 2. The implantable member 12 may be a cured implant shell, such as a conventional, relatively smooth-surfaced, silicone-based elastomeric implant shell, for example, a shell intended to be filled with silicone gel or saline and used as a breast prosthesis.

Figure 3:

A curable fluid composition 14, as described elsewhere herein, is applied to the outer surface of the shell 12. FIG. 3 shows a partial cross sectional view of a shell 12 having a composition coating 10. This may be accomplished by dipping the shell (as shown by shaded line 13), while the shell is fixed to a mandrel (not shown) into a solution bath containing the curable fluid composition 14 (FIG. 1A). The composition 14 comprises a silicone-based mixture including a solvent, and a leachable agent, as described elsewhere herein. The step of applying the composition 14 to the shell 12 may be accomplished by any suitable means of application, such as dipping and spraying.

Next, the composition coating is allowed to stabilize on the shell 12. For example, the shell 12 can be held in a stable position until the composition coating no longer flows freely. This occurs as some of the solvent evaporates from the coating, raising its viscosity. It can be appreciated that the step of allowing the composition to stabilize may be accomplished by various means, for example, by allowing some of the solvent to evaporate out of the composition or allowing a chemical reaction to occur, inducing precipitation of the soluble components. Alternatively, stabilization can be achieved during crosslinking of polymerization of the silicone, or precipitation of the silicone or pore-forming material. Also, a combination of the above-mentioned methods may be used for stabilization of the composition coating.

Figure 4:
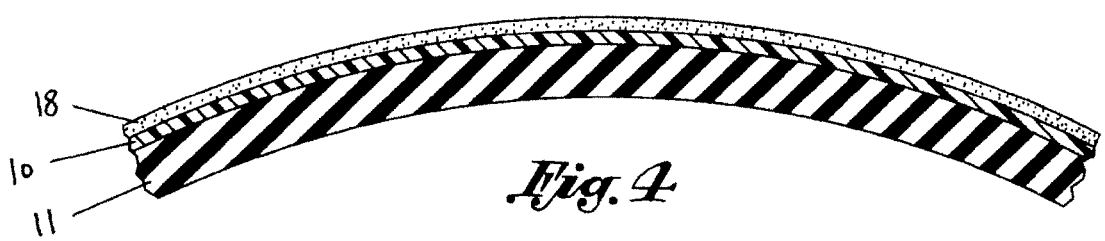

Once the composition 14 has stabilized on the shell 12, the second step is to immerse (see shaded line 15) the shell 12 in a particle bath 16 to apply particles to the composition coating on the shell 12 (FIG. 1B). The particles 18 applied to a composition-coated shell 12 is depicted in FIG. 1B. FIG. 4 shows a partial cross sectional view of a shell 12 with a composition coat 10 and particles 18. Application of the particle coating onto the shell 12, is performed while the composition coating on the shell 12 is still tacky and able to retain the particles. Stabilizing the composition prior to particle application may be accomplished by allowing at least some of the solvent in the composition to evaporate out of the composition until the composition is stable and tacky but not fully cured. Another method, in accordance with one aspect of the invention, for stabilizing the composition is provided in the Example below.

Steps one and two can be repeated before the leaching step is carried out, as indicated by shaded line 17. The steps of applying a curable fluid composition and applying a particle coating can be repeated, for example, one or more times, for example, three, five or even up to 20 times, until a final coating is applied. The final coating may be a particle or a composition coating.

After the final coating of particles or fluid composition is applied to the shell, the coated shell is then subjected to suitable curing conditions to solidify the composition with the particles embedded therein.

In the leaching step 19 (FIG. 1C), which takes place after the solidification step described above, the embedded particles and leachable agent in the composition coating are immersed in a leaching bath 20 and removed. After the removal of the particles, what remains is a network of interconnected pores 21 (the structure may include both relatively large pores and relatively smaller pores, for example, micropores) on the shell.

Figure 7:
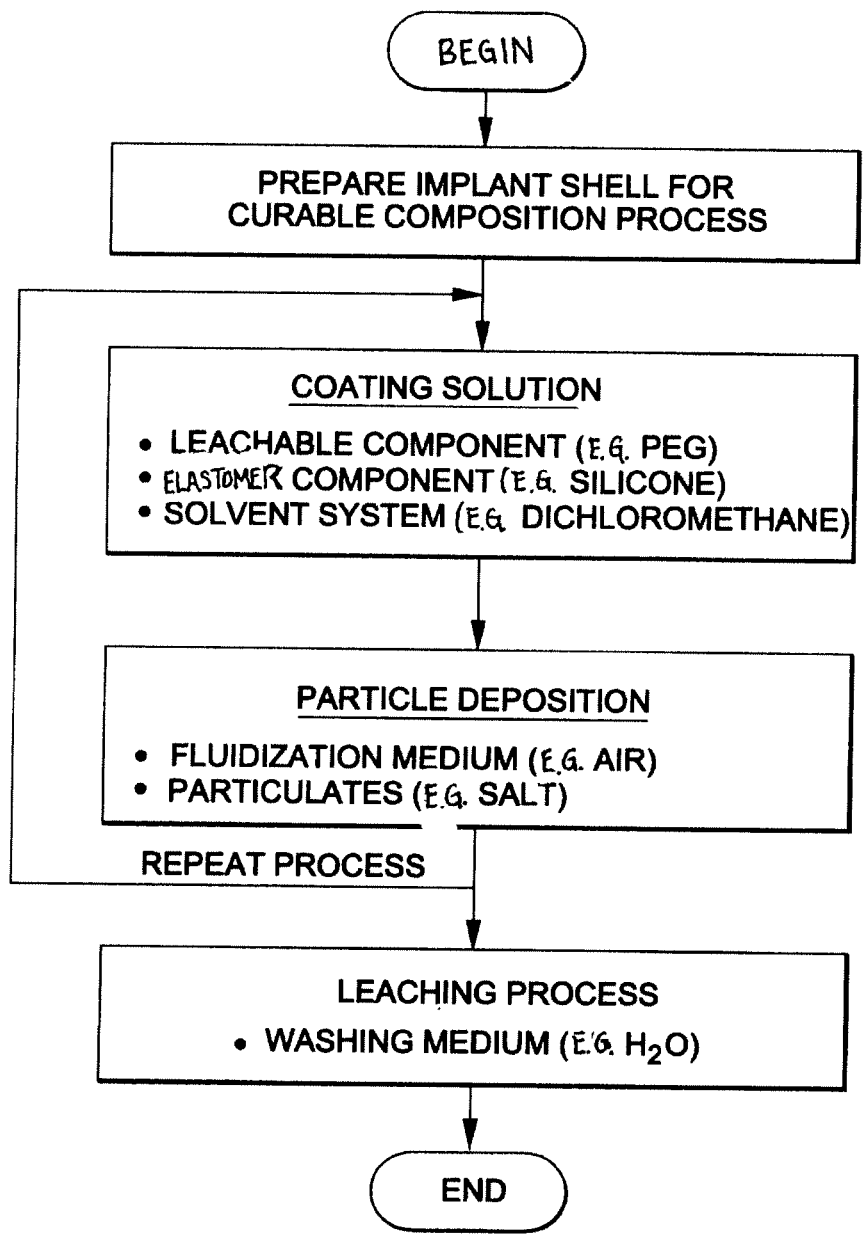
FIG. 7 is a simplified flow chart showing steps in a method for manufacturing an implant shell in accordance with an embodiment of the invention.

Also see FIG. 7 for a flow chart of the process described herein.

EXAMPLE 1

A mixture of about 7.5 wt. % PVA 2000 in water and about 40 wt. % acetoxy RTV silicone in xylene in a 3:1 volumetric ratio is prepared and homogenized for 30 seconds. An acetyl mandrel is placed into the mixture and coated uniformly as in a standard dip-coating process for the manufacturing of breast implant shells. The mandrel is then placed into a fluidized bed reactor with salt granules until no more granules can be deposited on the mandrel (about 5-10 seconds). This addition of salt particles tends to dry and stabilize the mixture by absorbing some of the water, thereby increasing the viscosity of the mixture. The coating is allowed to stabilize further at either 90° C. for about 15 minutes or at room temperature for about ½ hour, or otherwise sufficiently such that the next layer of composition may be applied. The procedure is repeated 3-5 times to obtain a coating of desired thickness.

Final curing may be performed at 165° C. for 2 hours, leaching with water or DCM for about 30 minutes for about 3 cycles with each (with agitation), and drying in vacuum overnight.

In one embodiment, a material is added to the composition before or after the composition has been applied to the shell, the material being effective to increase the viscosity of the composition, for example, by absorbing some of the solvent. When the leachable agent is in water, for example, a salt can be added in order to dry/stabilize the phase by absorbing the solvent. Other materials that may be helpful in this regard include sugars and other appropriate materials that can accelerate removal of solvent from the composition.

Next, a particle coating is applied to the composition to form the pores or cavities in the final elastomer foam structure. Application of the particles may be accomplished by any suitable means, for example, by sprinkling and pressing the particles into the tacky composition coating, or by immersing the tacky, coated shell in a bath of the particles. In the example shown, the particles are applied by immersing the coated shell into a fluidized bath 18 comprising a fluidization medium 19, for example, air, and particulates, for example, salt particles.

In some embodiments, the steps of applying the curable fluid composition and applying the particle coating are then repeated one or more times, for example, from about 0.5 up to about 20 times, for example, about 1 to about 10 times, for example, about 2 to about 5 times.

In one aspect of the invention, the particle coatings applied to the composition coatings may comprise coatings of particles having relatively different dimensions, one layer from the other. In other words, a first layer of particles may be relatively fine particles and a second layer of particles may be relatively coarse particles, or vice versa.

It is contemplated that in some embodiments, interconnectivity between pores may be increased or controlled by causing the particulates in the particle layer to fuse together. For example, in the event that the particles are salt crystals, application of moist heat may be effective increase interconnectivity thereof. Alternatively or additionally, an appropriate amount of a solvent for the particle material may be applied in order to cause the particles to fuse together. Further information which may be useful in appreciating this aspect of the invention may be found in copending, commonly owned U.S. Provisional Patent Application No. 61/177,955, filed on May 13, 2009 and entitled: IMPLANTS AND METHODS FOR MANUFACTURING SAME, the entire disclosure of which is incorporated herein by this reference.

Figure 5:
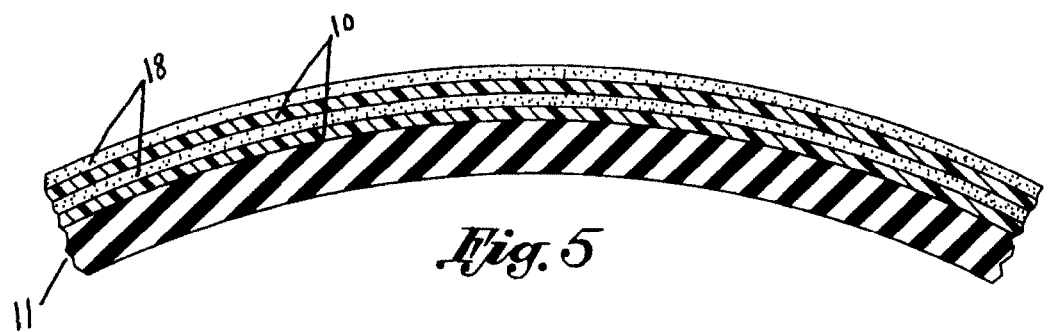

For example, in one embodiment, the steps of applying alternating particle and compositions coatings includes applying a first layer of the curable fluid composition to the shell, applying a first layer of particles, for example, relatively small particles, to the composition, applying a second layer of the composition to the first layer of particles, applying a second layer of particles, for example, relatively larger particles, to the second layer of the composition. FIG. 5 is a cross sectional view of a shell showing alternating layers of compositions coatings 10 and particle coatings 18. In a specific embodiment, the first layer of particles comprises particles having an average size in a range of between about 30 microns to about 150 microns, and the second layer of particles comprises particles having an average size in a range of between about 100 microns to about 450 microns. In yet other embodiments, the method further includes applying a third layer of the composition to the second layer of particles, and optionally, providing a third layer of particles, to the third layer of composition. The third layer of particles may have an average size in a range of between about 250 microns to about 750 microns.

The layered, coated shell is then subjected to suitable curing conditions to solidify and further stabilize the composition with the particles embedded therein.

Figure 6:
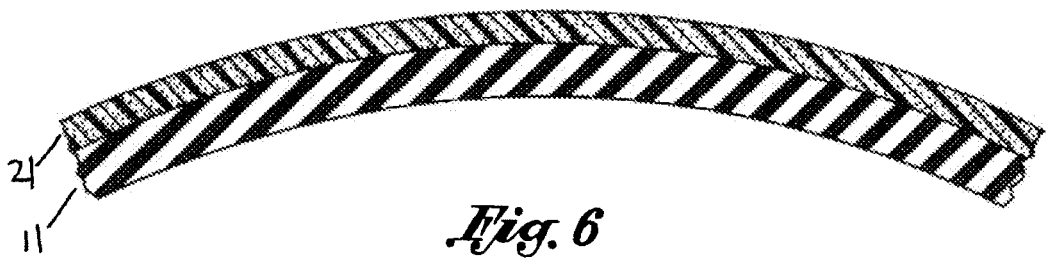

Next, the particles and leachable agent are then removed from the cured coating, thereby revealing a network of highly interconnected pores within the cured elastomer. FIG. 6 shows the partial cross sectional view of the shell 11 with a network of interconnected pores 21 after the removal of the particles. The step of removing the particles may comprise causing the particles to dissolve or contacting the particles with an abrasive surface. In the same step or in a different step, the leachable agent in the composition layers are removed from the elastomer.

In some embodiments, a conventional gas foaming process is used in addition to one or more of the presently described processes of the invention. For example, prior to the steps of applying the composition to the shell, the composition may be aerated by passing a gas, for example, air, through the composition to aerate the composition and create bubbles therein. Advantageously, any surface skin that may begin to form on the aerated composition coating would be opened up during extraction of the leachable phase to reveal highly interconnected pores resulting from the leachable materials, the particulates and the gas bubbles.

Removal of the particles and leachable agents may be accomplished by extracting these materials by exposing the layers to one or more suitable mediums capable of dissolving the particles and/or leachable agents. For example, the coated shell is dipped or submerged in a leaching bath 19 (FIG. 1C). The leaching bath may comprise water or an aqueous solution containing an agent capable of dissolving, leaching or otherwise removing the leachable agent and/or particles while leaving the cured elastomer substantially intact.

In some embodiments, the particles which are typically larger than the dispersed leachable agent, serve to create pores in the cured elastomer and the dispersed leachable agent serves to create micropores or interconnections between the relatively larger pores.

The resulting open-cell structure is believed to facilitate tissue ingrowth, improve fixation or adhesion of the implant and discourages organization of the collagen capsule which forms about the implant, which may help reduce capsular contraction.

In another aspect of the invention, an implantable composite member is provided in which the composite member has an external surface at least a portion of which is an open-cell porous structure, the composite member being made by one of the processes described herein.

In yet other embodiments of the invention, each of the first and second layers of particles are made up of substantially uniformly sized/shaped particles. In another aspect of the invention, each of the first and second layers of particles are made up of differently sized or shaped components.

After finishing the shell according to the steps described above, the steps required to make a finished mammary prosthesis may be conventional. First, any opening left by the mandrel support is patched with uncured silicone elastomer sheeting. If the prosthesis is to be filled with silicone gel, this gel is added and cured, the filled prosthesis packaged, and the packaged prosthesis sterilized. If the prosthesis is to be inflated with a saline solution, a valve is assembled and installed, the prosthesis is post cured if required, and the prosthesis is then cleaned, packaged and sterilized. A combination silicone/saline mammary prosthesis can also be made.

A method has been described for creating an outer layer having an open-cell structure in a silicone elastomer member. More specifically, the method can be applied to create a medical implant with an external surface layer of silicone elastomer having an open-cell structure, to create strips having a textured surface for control of scar formation, or to improve a process for making mammary prostheses. The product made by this method has also been described and is expected to have great utility in reducing capsular contraction, in preventing or controlling scar formation, and in anchoring medical implants.

Scar tissue formation in the healing of a wound or surgical incision is also a process involving the growth of fibrous tissue. A visible scar results from this healing process because the fibrous tissue is aligned in one direction. However, it is often aesthetically desirable to prevent scar formation, especially in certain types of plastic surgery. A member having an open-cell structure surface made in accordance with the present invention can be placed subcutaneously within a healing wound or incision to prevent the fibrous tissue from aligning and thereby prevent or reduce scar formation.

It is often important to anchor medical implants against movement. Mammary prostheses are one example of implants that must be anchored. Facial implants are another example of implants that must be anchored. With facial implants it is particularly important that they be anchored securely against movement because of their prominent location. Providing such implants with an open-cell structure surface made in accordance with the present invention is a particularly advantageous way to ensure that they will be anchored securely.

EXAMPLE 2

A composition is prepared by mixing polyethylene glycol monomethyl ether (2000 Da), which will serve as a leachable agent, with a low viscosity silicone elastomer dispersion, for example, (e.g. polydimethylsiloxane, polydiphenylsiloxane, poly(dimethylsiloxane-co-diphenylsiloxane), poly(dimethylsiloxane-ran-diphenylsiloxane), etc.), in an organic solvent (e.g. xylene), and at about 5 to about 40 wt %, or in some specific embodiments, 17, 25 and 35 wt % of acetoxy RTV silicone. This composition is applied to the surface of an elastomeric shell held on a mandrel or other mechanical support. The layer is allowed to evaporate most of the solvent off.

A coating of sodium chloride crystals (about 250 μm to about 850 μm size) are applied to the tacky composition layer by submerging the coated shell into a fluidized bath of salt and air. This forms a relatively uniformly distributed single layer particle coating.

The elastomer is allowed to evaporate the solvent off and subsequently cured at approximately 145° C.

The coated shell is then submerged in an aqueous washing medium at approximately 40° C. and gently agitated to remove the particles and leachable agent.

EXAMPLE 3

The same process is performed as in Example, 1, except that the composition is a mixture of 10 mL xylene, 10 mL DCM, 5 mL by dry volume PEG 2000 and 5 mL by dry volume acetoxy RTV silicone elastomer.

EXAMPLE 4

The same process is performed as in Example 2, except that the composition is a mixture of 5 mL water
1 mL xylene
0.5 mL by dry volume PVA 1500
0.2 mL by dry volume RTV.

In another aspect of the invention, an article, for example a thin, flexible sheet, useful as a laminate, is provided. More specifically, the present invention provides a biocompatible sheet suitable for use as a laminate on an implantable device or object, in order to enhance tissue adhesion or ingrowth when the implantable device or object is implanted in a patient. Thus, the manufacture of the materials in accordance with the invention is not limited to conventional dipping processes but may be made by other suitable means, for example, through the lamination of a sheet that is prepared by molding or casting. For example, it is contemplated by the inventors that a sheet or laminate can be prepared by casting the fluid material with all the components present in various ratios (DCM, PEG)+(Xylene, RTV), and in some instances, mixed and shaken with the particulate component, for example, salt crystals added to the liquid. The particulate and fluid mixture can be shaken or mixed and cast onto a substrate or into a mold cavity. In some embodiments, the particulate component comprises salt in a range of about 10% to about 99% of total dissolved solids. In a more specific embodiment, the salt is present at about 25% to about 60%. It can be appreciated that different amounts and different particle sizes/shapes of salt will produce laminates having different porosities. Once cured, the laminate can be laminated, by any conventional means known in the art, onto a medical device or implant or other object to be implanted in a body, for example, any object or device which would be improved by the addition of such a laminate on one or more surfaces of the object or device. For example, the sheet may be laminated to catheter cuffs for long term implantable catheters, dura-matter substitutes or the like.

EXAMPLE 5

A laminate for an implant is prepared as follows. A fluid composition made up of 10 mL xylene, 10 mL DCM, 5 mL by dry volume PEG 2000 and 5 mL by dry volume acetoxy RTV silicone elastomer is mixed with 3.5 mL by volume salt particles. This mixture is shaken together to ensure substantially uniform distribution of particles. The mixture is cast molded by applying the mixture to a mold surface to form a layer having a uniform thickness of between about 1 mm to about 5 mm. The layer is allowed stabilize and is cured at about 120° C. for a sufficient period of time. The cured sheet is removed from the mold surface and is then contacted with a gentle spray of pure water to remove all of the leachable components and salt particles. The resulting, thin, flexible, porous silicone foam sheet is then further processed and sterilized and packaged for sale or storage for later use as a laminate on a surface of an implantable device.

EXAMPLE 6

The process of Example 5 is performed with the additional steps of repeating, three times, the step of applying a fluid composition/particulate mixture to the stabilized layer prior to the step of curing. The final thin, flexible sheet is a multi-layered sheet and, in this example, has a thickness of greater than about 5 mm.

EXAMPLE 7

The process of Example 5 is performed, however the cured stabilized sheet is not contacted with a spray of water to remove the leachable agents and particulates before being packaged for sale or storage. Instructions are provided with regard to: removing the leachable agents and particulates, sterilization, and bonding the sheet to a surface of a medical device.

EXAMPLE 8

The process of Example 5 is performed to make two square sheets of uncured foam, approximately 240 mm×240 mm. A layer of silicone adhesive in DCM is applied, by spraying or brushing, to one side of each of the sheets. The sheets are stretched uniformly and positioned one on top of the other, adhesive side facing each other, over a newly molded breast implant shell filled with silicone or air. The foam sheets are joined together at the edge of the implant and affixed by suitable clamps at the perimeter of the implant. Twenty four hours later, the clamps are removed. Excess foam is die-cut away from the implant by a press. The implant/foam is exposed to 140° C. for 2.5 hours for final post-curing.

While this invention has been described with respect to various specific examples and embodiments, it is to be understood that the invention is not limited thereto and that it can be variously practiced within the scope of the invention.

What is claimed is:

1. A method of making a shell of an implantable breast prosthesis having a textured surface, the method comprising the steps of:
   (a) providing an implantable shell;
   (b) applying a curable fluid composition to the shell, the composition comprising a mixture containing an elastomer component, a leachable agent comprising a water soluble polymer in the form of droplets in the mixture, and a solvent component;
   (c) applying a layer of particles to the composition;
   (d) allowing the composition to stabilize; and
   (e) removing the particles and the leachable agent from the stabilized composition, to form a composite material having an external surface at least a portion of which is an open-cell porous structure defined by relatively large pores left by the removed particles and relatively smaller pores, forming connections between the relatively large pores, left by the removed leachable agent.

2. The method of claim 1 wherein the solvent component includes a solvent selected from the group consisting of xylene, pentane, hexane, dichloromethane (DCM), dimethyl sulfoxide, dioxane, NMP, DMAc, and combinations thereof.

3. The method of claim 1 wherein the mixture is an emulsion.

4. The method of claim 1 wherein the particles comprise a material selected from the group of materials consisting of sodium chloride, barium sulfate, potassium nitrate, and sodium carbonate.

5. The method of claim 1 wherein the particles are substantially round.

6. The method of claim 1 wherein the leachable agent is in the form of droplets having diameters in a range of between about 50 microns to about 400 microns.

7. The method of claim 1 wherein the particles have an average particle size in a range of between about 100 microns to about 900 microns.

8. The method of claim 1 further comprising the step of repeating steps (b) and (c) prior to the step of removing, to form a layered structure.

9. The method of claim 1 wherein the particles are angular in shape such that the porous structure is defined by relatively large angular pores left by the removed particles and relatively smaller pores, forming connections between the relatively large angular pores, left by the removed droplets.

10. A method of making a shell of an implantable breast prosthesis having a textured surface, the method comprising the steps of:
   (a) providing an implantable shell;
   (b) applying a curable fluid composition to the shell, the composition comprising a mixture containing an elastomer component, a leachable agent in the form of droplets in the mixture, and a solvent component;
   (c) applying a layer of particles to the composition;
   (d) allowing the composition to stabilize; and
   (e) removing the particles and the leachable agent from the stabilized composition, to form a composite material having an external surface at least a portion of which is an open-cell porous structure defined by relatively large pores left by the removed particles and relatively smaller pores, forming connections between the relatively large pores, left by the removed leachable agent;

wherein the leachable agent is an agent selected from the group of agents consisting of polyvinyl alcohol, polyethylene glycol, polyacrylic acid, polymethacrylate, poly-lactide, polyglycolide, polycaprolactone, polydioxanone, derivatives thereof, blends thereof, copolymers thereof, terpolymers thereof, and combinations thereof.

11. The method of claim 10 wherein the leachable agent is in the form of droplets having diameters in a range of between about 50 microns to about 400 microns.

12. The method of claim 10 wherein the solvent component includes a solvent selected from the group consisting of xylene, pentane, hexane, dichloromethane (DCM), dimethyl sulfoxide, dioxane, NMP, DMAc, and combinations thereof.

13. The method of claim 10 wherein the mixture is an emulsion.

14. The method of claim 10 wherein the particles comprise a material selected from the group of materials consisting of sodium chloride, barium sulfate, potassium nitrate, and sodium carbonate.

15. The method of claim 10 further comprising the step of repeating steps (b) and (c) prior to the step of removing, to form a layered structure.

16. A method of making a shell of an implantable breast prosthesis having a textured surface, the method comprising the steps of:
(a) providing an implantable shell;
(b) applying a curable fluid composition to the shell, the composition comprising a mixture containing an elastomer component, a leachable agent in the form of droplets in the mixture, and a solvent component;
(c) applying a layer of particles to the composition;
(d) allowing the composition to stabilize; and
(e) removing the particles and the leachable agent from the stabilized composition, to form a composite material having an external surface at least a portion of which is an open-cell porous structure defined by relatively large pores left by the removed particles and relatively smaller pores, forming connections between the relatively large pores, left by the removed leachable agent, wherein the step of removing comprises contacting the stabilized composition with a solvent for the particles and the leachable agent.

17. The method of claim 16 wherein the particles are angular in shape such that the porous structure is defined by relatively large angular pores left by the removed particles and relatively smaller pores, forming connections between the relatively large angular pores, left by the removed droplets.

18. The method of claim 16 wherein the solvent component includes a solvent selected from the group consisting of xylene, pentane, hexane, dichloromethane (DCM), dimethyl sulfoxide, dioxane, NMP, DMAc, and combinations thereof.

19. The method of claim 16 wherein the mixture is an emulsion.

20. The method of claim 16 wherein the particles comprise a material selected from the group of materials consisting of sodium chloride, barium sulfate, potassium nitrate, and sodium carbonate.

* * * * *